(12) United States Patent
Amiri Farahani et al.

(10) Patent No.: US 9,131,915 B2
(45) Date of Patent: Sep. 15, 2015

(54) METHOD AND APPARATUS FOR NOISE CANCELLATION

(75) Inventors: Mohsen Amiri Farahani, Fredericton (CA); Eduardo Castillo Guerra, Fredericton (CA); Bruce G. Colpitts, Fredericton (CA); Anthony W. Brown, Fredericton (CA)

(73) Assignee: University of New Brunswick, Fredericton, New Brunswick (CA)

( * ) Notice: Subject to any disclaimer, the term of this patent is extended or adjusted under 35 U.S.C. 154(b) by 504 days.

(21) Appl. No.: 13/543,658

(22) Filed: Jul. 6, 2012

(65) Prior Publication Data

US 2013/0011144 A1 Jan. 10, 2013

Related U.S. Application Data

(60) Provisional application No. 61/504,879, filed on Jul. 6, 2011.

(51) Int. Cl.
| | |
|---|---|
| *A61B 6/00* | (2006.01) |
| *G01D 5/353* | (2006.01) |
| *A61B 5/0402* | (2006.01) |
| *G01D 3/032* | (2006.01) |
| *A61B 5/00* | (2006.01) |

(52) U.S. Cl.
CPC .......... *A61B 6/5258* (2013.01); *G01D 5/35364* (2013.01); *A61B 5/0402* (2013.01); *A61B 5/725* (2013.01); *G01D 3/032* (2013.01)

(58) Field of Classification Search
CPC .............. H04L 27/01; H04L 25/03006; H04L 25/03019; H04L 25/03057
USPC .................................. 375/232, 348, 346, 349
See application file for complete search history.

(56) References Cited

U.S. PATENT DOCUMENTS

| | | | |
|---|---|---|---|
| 4,238,746 A | 12/1980 | McCool et al. | |
| 4,649,505 A | 3/1987 | Zinser, Jr. et al. | |
| 4,658,426 A | 4/1987 | Chabries et al. | |
| 4,742,548 A | 5/1988 | Sessler et al. | |

(Continued)

FOREIGN PATENT DOCUMENTS

| | | |
|---|---|---|
| CA | 2151715 A1 | 6/1994 |
| CA | 2247293 | 4/1999 |

(Continued)

OTHER PUBLICATIONS

W. Brown et al., "Dark-pulse Brillouin optical time domain sensor with 20-mm spatial resolution," J. Lightw. Technol., vol. 25, No. 1, 381-386, Jan. 2007.

(Continued)

*Primary Examiner* — Kevin Kim
(74) *Attorney, Agent, or Firm* — Eugene F. Derényi; Fogler, Rubinoff LLP

(57) ABSTRACT

Method and apparatus of denoising recurrent signals comprising: providing first and second noisy signals each comprising a deterministic signal and (different realizations of) white noise; selecting one of the noisy signals as an input signal and the other noisy signal as a desired signal; providing an estimate of the deterministic signal in the input signal; determining the error between the estimated deterministic signal and the desired signal; adjusting the estimate of the deterministic signal using the error and producing an adjusted estimate of the deterministic signal.

9 Claims, 16 Drawing Sheets

(56) References Cited

U.S. PATENT DOCUMENTS

| | | | |
|---|---|---|---|
| 5,226,076 | A | 7/1993 | Baumhauer, Jr. et al. |
| 5,602,928 | A | 2/1997 | Eriksson et al. |
| 5,953,380 | A * | 9/1999 | Ikeda ............................ 375/346 |
| 6,094,623 | A | 7/2000 | Mintchev et al. |
| 6,278,786 | B1 | 8/2001 | McIntosh |
| 6,781,521 | B1 * | 8/2004 | Gardner et al. ............ 340/854.4 |
| 6,917,688 | B2 | 7/2005 | Yu et al. |
| 6,940,982 | B1 | 9/2005 | Watkins |
| 6,954,771 | B2 | 10/2005 | De Clippel |
| 7,092,529 | B2 | 8/2006 | Yu et al. |
| 7,474,915 | B2 | 1/2009 | Assaleh et al. |
| 7,657,038 | B2 | 2/2010 | Doclo et al. |
| 7,885,417 | B2 | 2/2011 | Christoph |

FOREIGN PATENT DOCUMENTS

| | | |
|---|---|---|
| CA | 2404030 A1 | 10/2001 |
| CA | 2481629 A1 | 3/2006 |
| CA | 2437477 C | 11/2008 |
| CA | 2692151 A1 | 1/2009 |
| CA | 2519868 C | 11/2012 |

OTHER PUBLICATIONS

B. Widrow et al., "Adaptive noise cancelling: Principles and applications," Proc. IEEE, vol. 63, No. 12, 1975, pp. 1692-1716.

Y. Kawamura and Y. Itoh, "A noise reduction method based on linear prediction with variable step-size," IEICE Trans. on Fundamentals of Electronics, Communications and Computer Sciences, vol. 88, pp. 855-861, Apr. 2005.

J. R. Zeidler, "Performance analysis of LMS adaptive prediction filters," Proc. IEEE, vol. 78, No. 12, Dec. 1990, pp. 1781-1806.

S. L. Gay, S. Tavathia, "The fast affine projection algorithm," Acoustics, Speech, and Signal Processing, 1995. ICASSP-95, vol. 5, 1995, pp. 3023-3026.

G. V. Moustakides, S. Theodoridis, "Fast Newton transversal filters-a new class of adaptive estimation algorithms," IEEE Trans. Signal Process., vol. 39, No. 10, pp. 2184-2193, 1991.

Procaznik and J. Holcik, "Dynamic adaptive recurrent filter for stress-test ECG processing," Int. Proc. IEEE, 1993, pp. 736-737.

Goldberger et al., "PhysioBank, PhysioToolkit, and PhysioNet: Components of a New Research Resource for Complex Physiologic Signals," Circulation 101(23): pp. e215-e220 [Circulation Electronic Pages: http://circ.ahajournals.org/cgi/content/full/101/23/e215]; Jun. 13, 2000.

L. Lin and D. Y. Chen, "Adaptive filter design using recurrent cerebellar model articulation controller," IEEE Trans. Neural Netw., vol. 21, No. 7, pp. 1149-1157, Jul. 2010.

Stapleton and S. Bass "Adaptive noise cancellation for a class of nonlinear dynamic reference channels," IEEE Trans. Circuits Syst., vol. 32, No. 2, pp. 268-271. 1985.

Pan and W. J. Tompkins, "A real-time QRS detection algorithm," IEEE Trans. Biomed. Eng., vol. 32, No. 3, pp. 230-236, 1985.

V. Bortolani et al., "Theory of Brillouin scattering from surface acoustic phonons in supported films," J. Phys. C: Solid State Phys. vol. 16, 1983.

J. Dhliwayo, et al., "Statistical analysis of temperature measurement errors in a Brillouin scattering-based distributed temperature sensor," Proc. SPIE, vol. 2838, 1996, pp. 276-286.

J. M. Gorriz, et al., "A novel LMS algorithm applied to adaptive noise cancellation," IEEE Signal Pr, pp. c. Letters, vol. 16, No. 1, pp. 34-37, 2009.

K. T. V. Grattan and T. Sun, "Fiber optic sensor technology: an overview," Sensors and Actuators, vol. 82, pp. 40-61, 2000.

M. A. Soto, et al., "Long-rang Brillouin optical time-domain analysis sensor employing pulse coding techniques," Meas. Sci. Technol., vol. 21, pp. 1-7, 2010.

M. D. Jones, "Using simplex codes to improve OTDR sensitivity," IEEE Photon. Tech. Letters, vol. 15, No. 7, pp. 822-824, 1993.

M. Horowitz, et al., "Broad-band transmitted intensity noise induced by Stokes and anti-Stokes Brillouin scattering in single-mode fibers," IEEE Photon. Tech. Letters, vol. 9, No. 1, pp. 124-126, 1997.

N. V. Thakor and Y. Zhu, "Applications of adaptive filtering to ECG analysis: noise cancellation and arrhythmia detection," IEEE Trans. Biomed. Eng., vol. 38, No. 8, pp. 785-794, 1991.

R. Martin and J. Altenhone "Coupled adaptive filters for acoustic echo control and noise reduction," Proc. ICASSP, vol. 5, pp. 3043-3046, 1995.

W. Guirong, et al., "Fiber optic displacement sensor and its signal processing," Proc. SPIE, vol. 2895, 1996, pp. 401-407.

Y. Wu, et al., "filtering electrocardiographic signals using an unbiased and normalized adaptive noise reduction system," Med. Eng. Phys., vol. 31, No. 1, pp. 17-26, 2009.

S. Haykin, Adaptive Filter Theory, 3rd edition, prentice Hall (1996), chapter 7 "Kalman Filters", 302-337.

S. Haykin, Adaptive Filter Theory, 3rd edition, prentice Hall (1996), chapter 13, Recursive least-Squares Algorithm, 562-588.

* cited by examiner

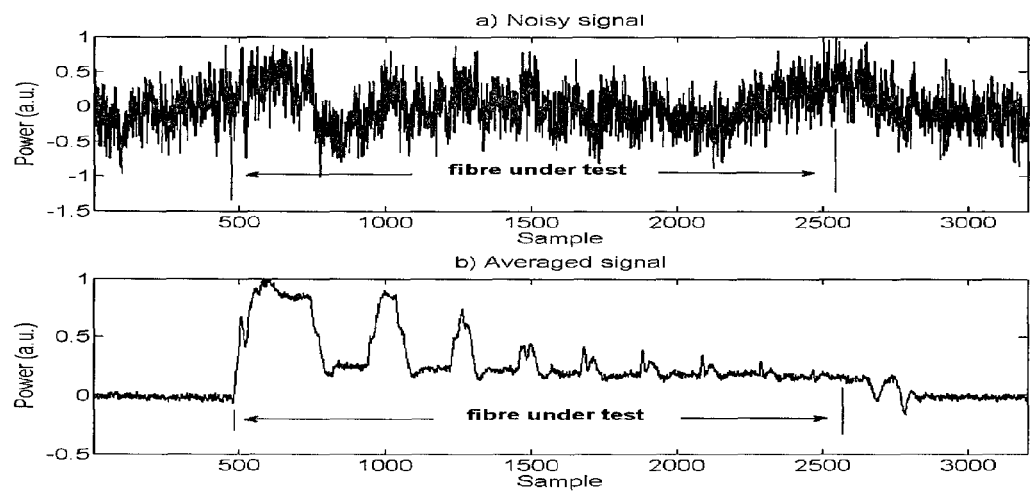
Figures 2a) and 2b)

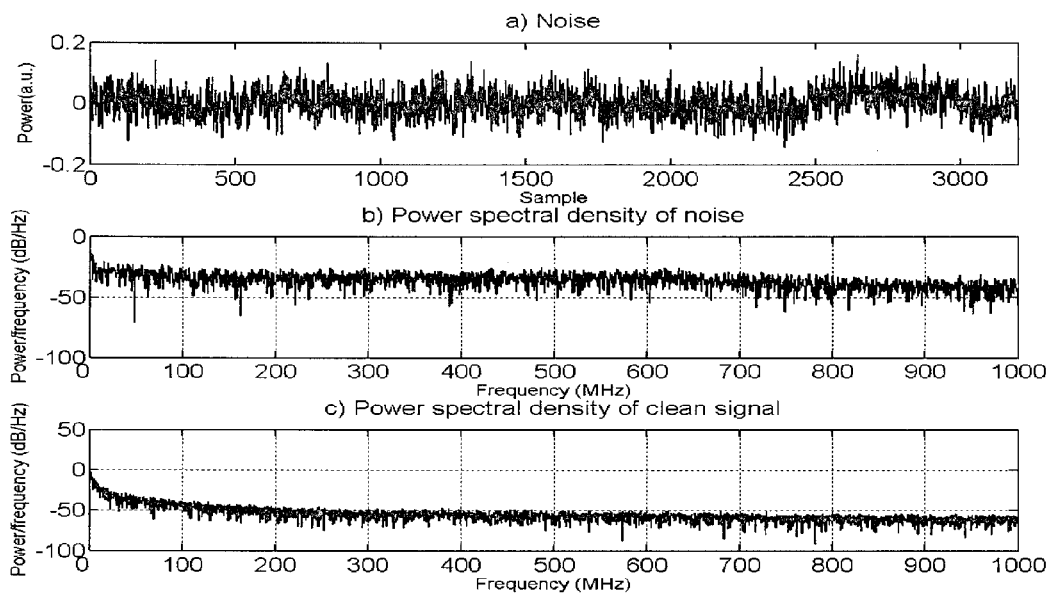
Figures 3a), 3b) and 3c)

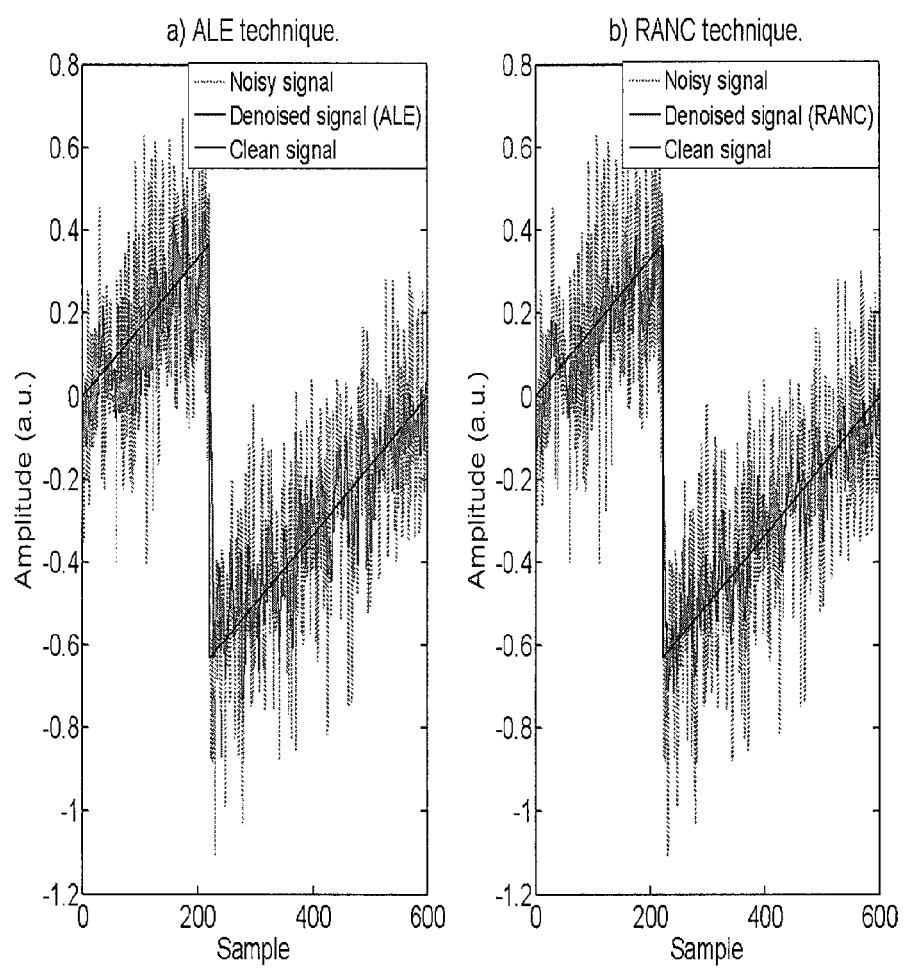
Figures 8a) and 8b)

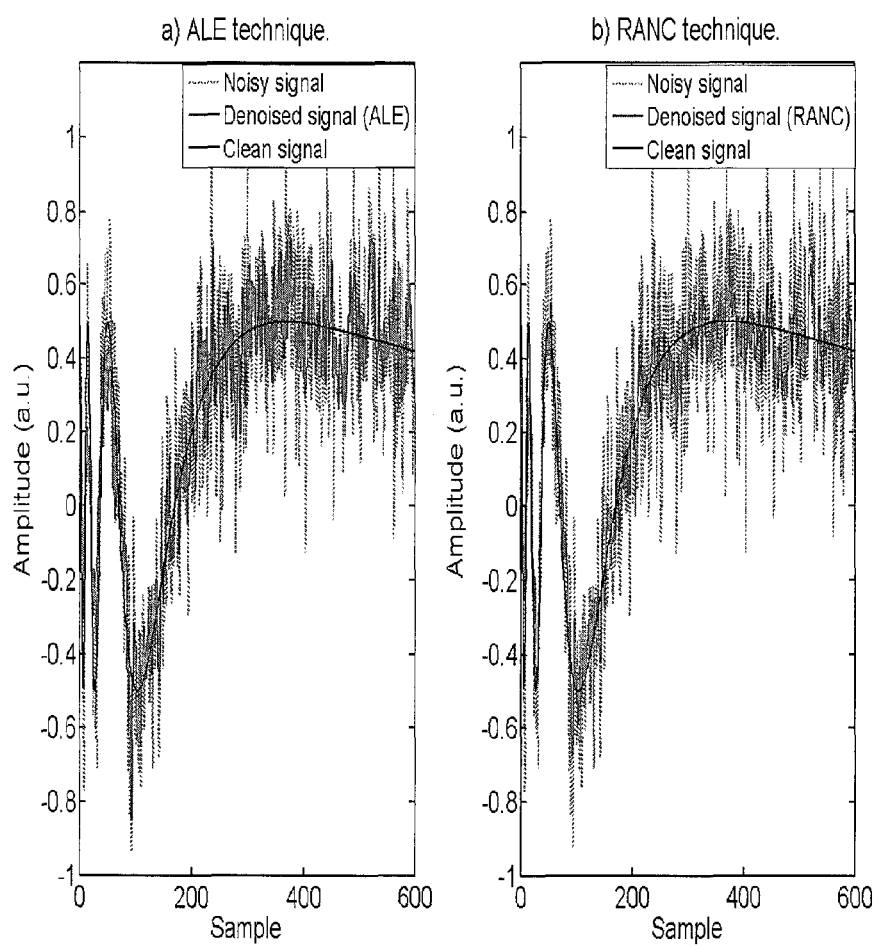
Figures 9a) and 9b)

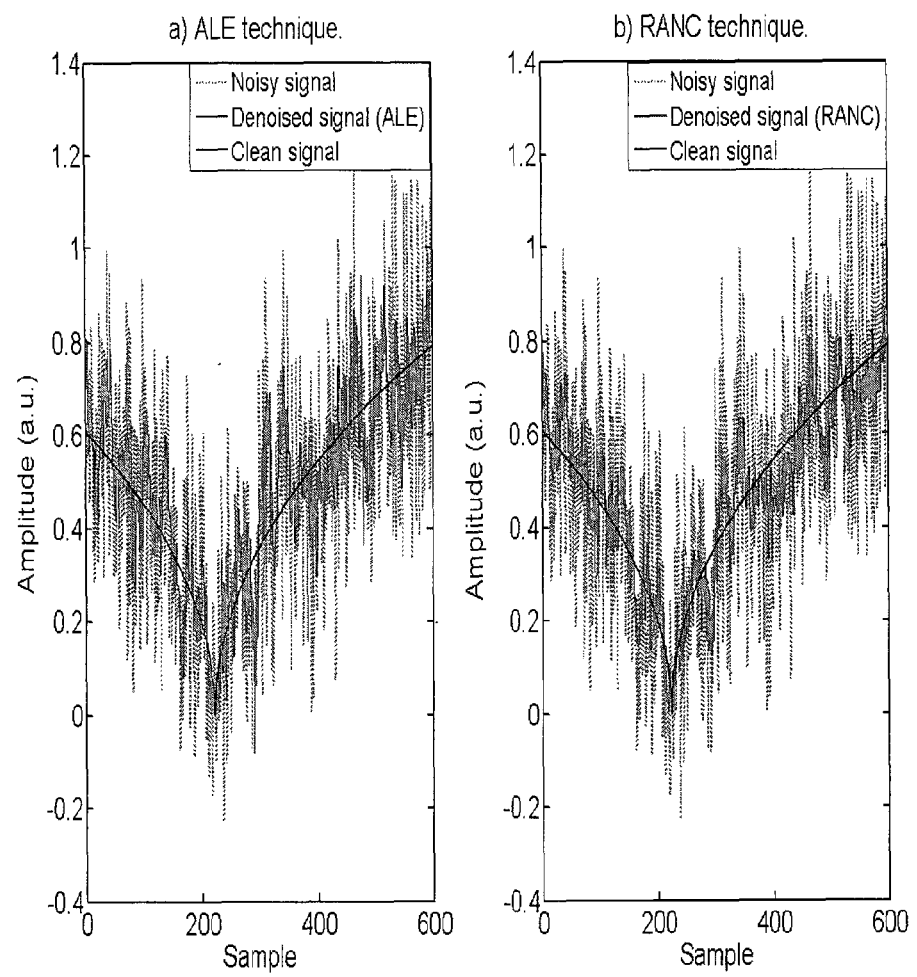
Figures 10a) and 10b)

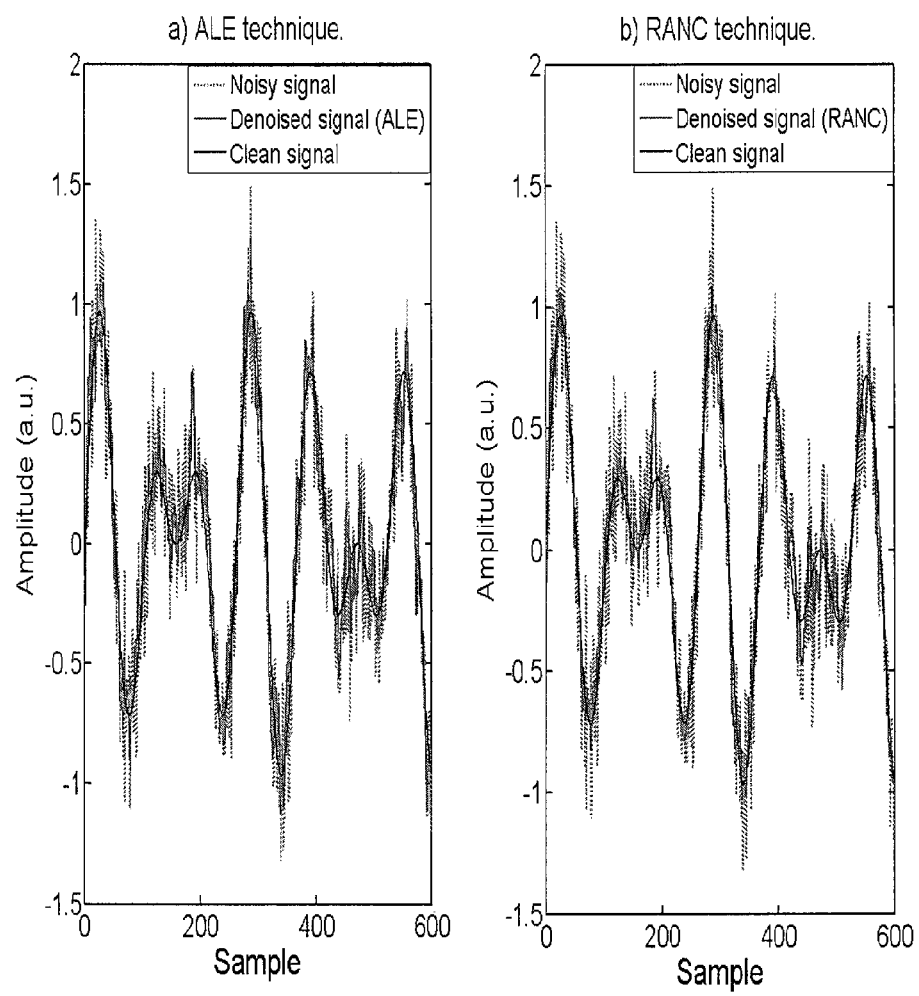
Figures 11a) and 11b)

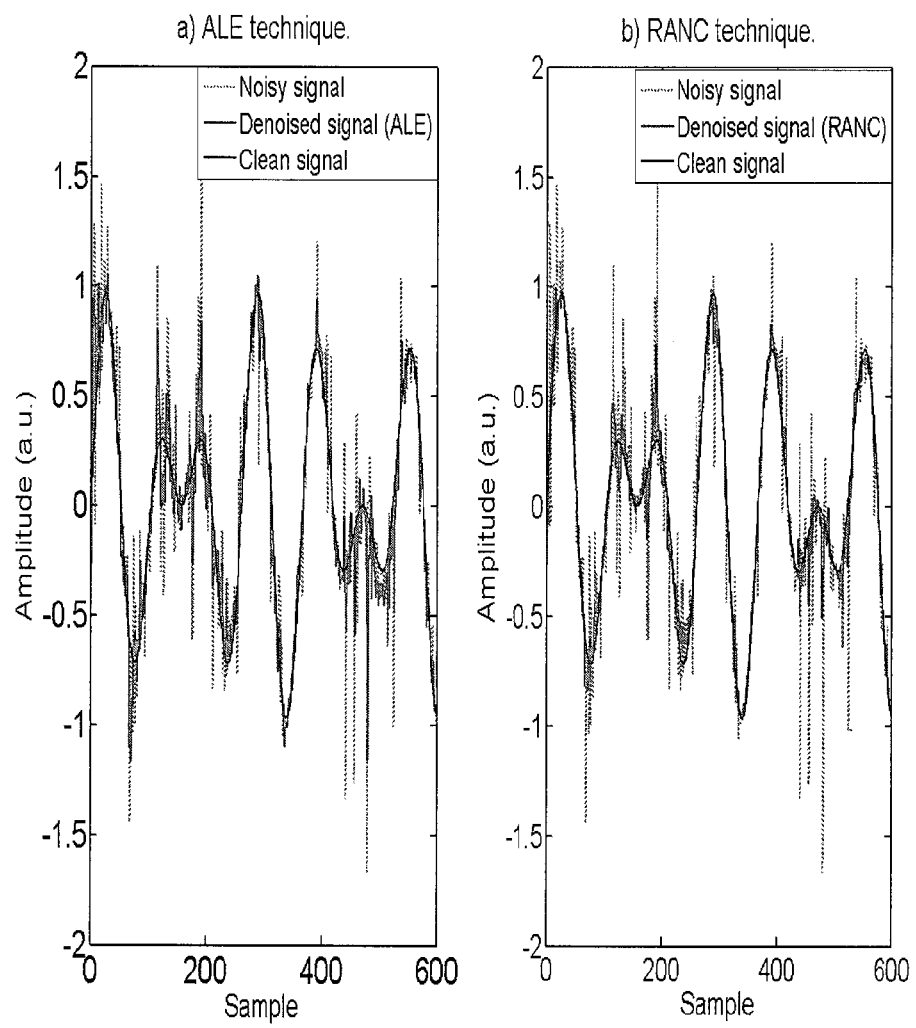
Figures 12a) and 12b)

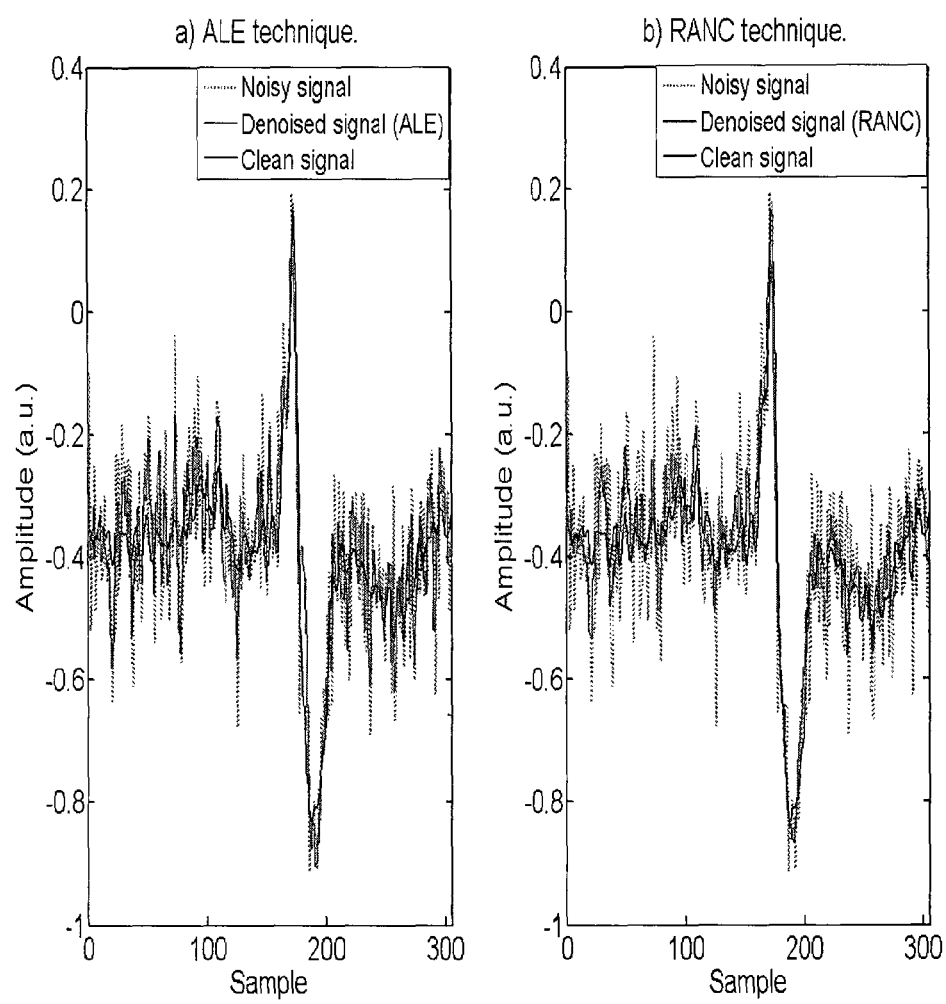
Figures 13a) and 13b)

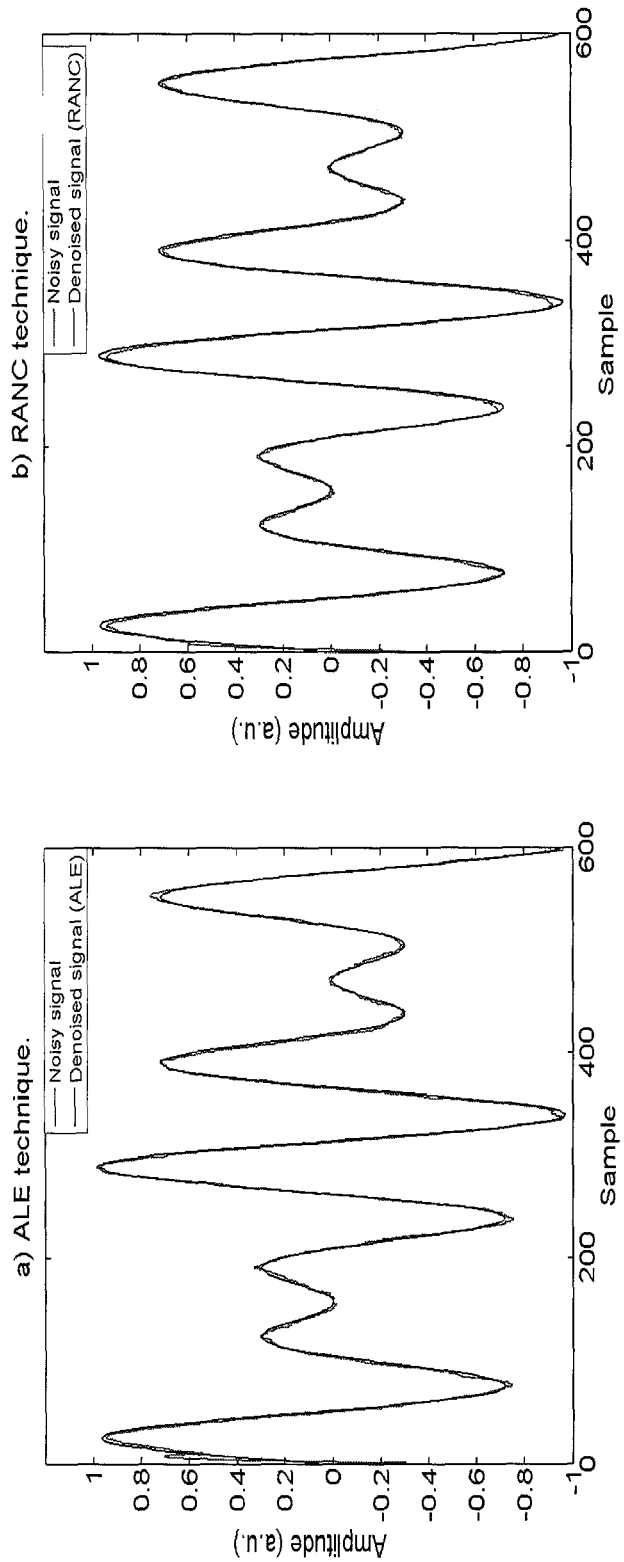
Figures 14a) and 14b)

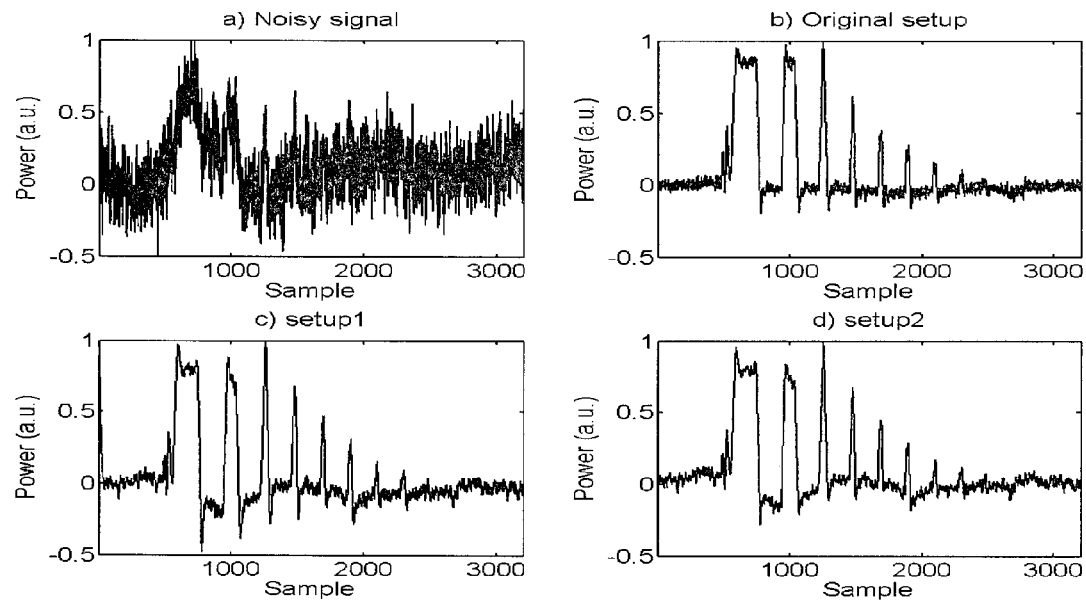
Figures 15a), 15b), 15c) and 15d)

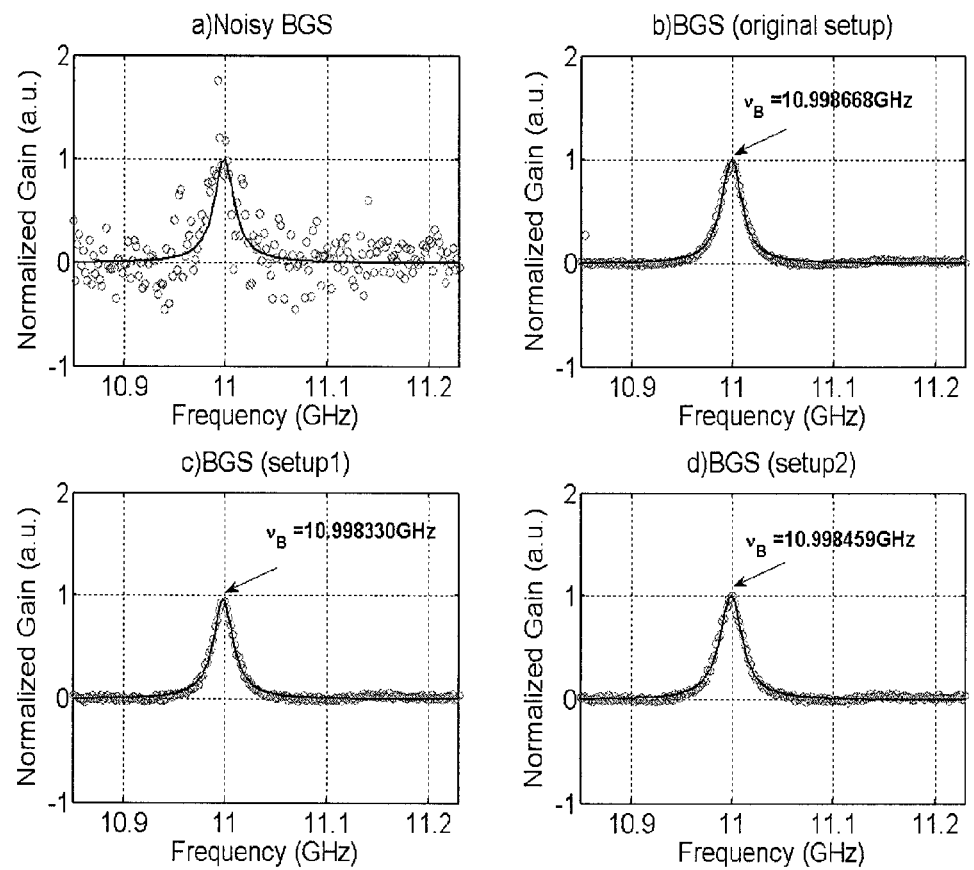
Figures 17a), 17b), 17c) and 17d)

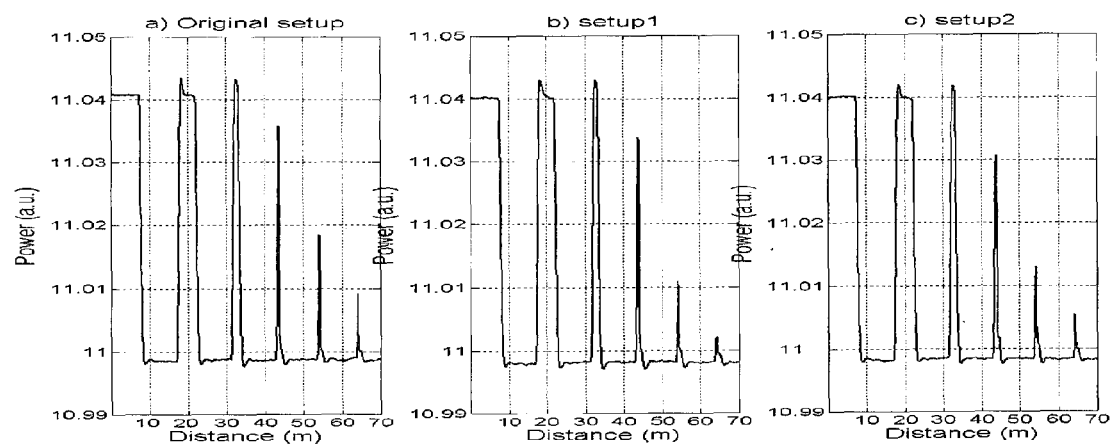
Figures 18a), 18b), and 18c))

METHOD AND APPARATUS FOR NOISE CANCELLATION

FIELD

The present invention relates to the field of noise cancellation in signals in general, and recurrent signals in particular.

BACKGROUND

Distributed optical fibre sensors based on stimulated Brillouin scattering ("SBS") have the ability to measure strain and temperature along many kilometers of optical fibre. SBS sensors have attracted a significant amount of research in the last few decades due to their competitive advantage of enabling continuous measurements over long distances and in hazardous environments.

Recurrent signals, particularly those collected from Brillouin optical time-domain analysis ("BOTDA") sensors contain noise. Eliminating noise, preferably as much noise as possible, from recurrent signals improves the signal-to-noise ratio of recurrent signals. Various methods have been proposed for denoising recurrent signals but can involve averaging many signals and may be a slow process.

SUMMARY

In one embodiment, the present invention relates to a method of denoising recurrent signals comprising providing first and second noisy signals each comprising a deterministic signal and a (different realization of) white noise; selecting one of the noisy signals as an input signal and the other noisy signal as a desired signal; providing an estimate of the deterministic signal in the input signal; determining the error between the estimated deterministic signal and the desired signal; adjusting the estimate of the deterministic signal using the error and producing an adjusted estimate of the deterministic signal.

The white noise in the first signal is different from the white noise in the second signal. The adjusting of the deterministic signal may be carried out by minimizing the error using a given criterion. The error may be minimized using an error minimization method, such as an error minimization method selected from the group consisting of least mean squares, normalized least mean squares, recursive least squares, affine projection, fast affine projection, fast Newton transversal and Kalman.

In another embodiment, the present invention relates to a method for denoising recurrent noisy signals using an improved adaptive noise cancellation method comprising providing a first noisy signal as the input signal; providing a second noisy signal as the desired signal, applying an adaptive filter to the input signal to produce an estimated deterministic signal of the input signal; determining an estimated clean signal by subtracting the output of the estimated deterministic signal of the input signal from the desired signal.

In another embodiment, the present invention relates to a method of adaptive noise cancellation comprising an adaptive filter; providing a first noisy signal as the input signal; providing a second noisy signal as the desired signal, estimating a clean signal by subtracting an output of the adaptive filter from the desired signal.

In another embodiment, the present invention relates to a brillouin analysis sensor system comprising a pump laser and a probe laser; a first circulator and a sensing fibre; the pump laser connected to the first circulator and the first circulator connected to the sensing fibre; a modulator, polarization control and a second circulator wherein the probe laser is connected to the modulator, the modulator is connected to the polarization control, the polarization control is connected to the second circulator, and the second circulator is connected to the sensing fibre; pulse generator; a pulse generator wherein the pulse generator is connected to the modulator; a detector. amplifier, digitizer, ensemble averaging module, denoising filter wherein the second circulator is connected to the detector, the detector is connected to the amplifier, the amplifier is connected to the digitizer, the digitizer is connected to the ensemble averaging module and the ensemble averaging module is connected to the denoising filter.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2a) is a graph of a normalized BOTDA signal;

FIG. 2b) is a graph of a normalized denoised BOTDA signal;

FIG. 3a) is a graph of typical noise in a BOTDA signal;

FIG. 3b) is a graph of power spectral density ("PSD") of the noise of FIG. 3a);

FIG. 3c) is a graph of PSD of a clean signal;

FIGS. 8a) and 8b) are the ramp waveform and the results of filtering for Ex. 1;

FIGS. 9a) and 9b) are the Doppler signal and the results of filtering for Ex. 2;

FIGS. 10a) and 10b) are the Cusp waveform and the results of filtering for Ex. 3;

FIGS. 11a) and 11b) are the sinusoidal waveform and the results of filtering for the first test of Ex. 4;

FIGS. 12a and 12b) are the sinusoidal waveform and the results of filtering for the second test of Ex. 4;

FIGS. 13a and 13b) are the electrocardiograph (ECG) signal and the results of filtering for Ex. 5;

FIGS. 14a) and 14b) are graphical results of averaging an ensemble of 40 signals denoised in Ex. 4 using the prior art ALE method, and a RANC method according to an embodiment of the present invention;

FIGS. 15a) through d) are a Noisy signal and denoised signals in the original and modified setups;

FIGS. 17a) through d) are BGSs and fitted Lorentzian curves for the original and modified setups;

FIGS. 18a) through c) are Brillouin frequency shifts (BFSs) along the fibre in the original and modified setups;

DETAILED DESCRIPTION

Figure 1:
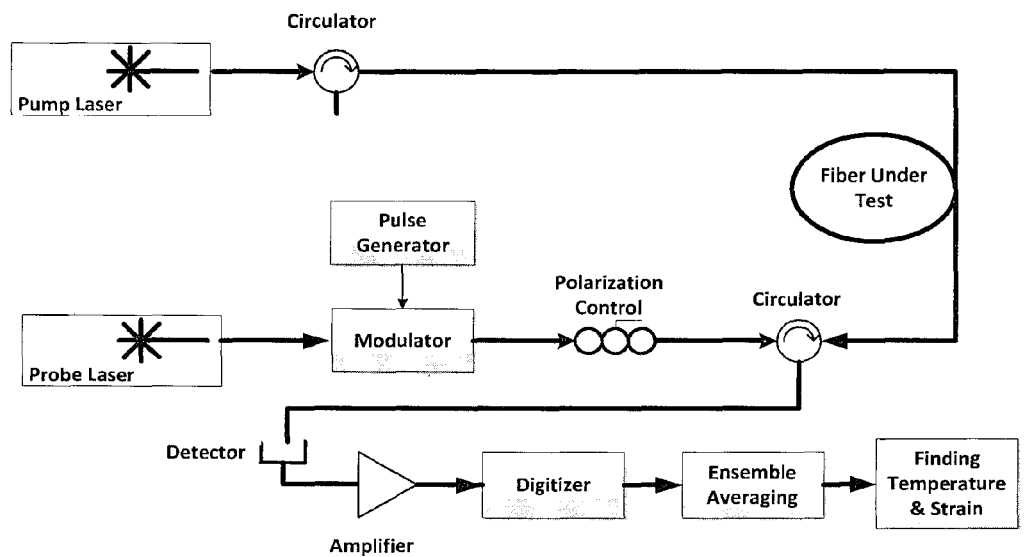
FIG. 1 is a schematic diagram of an example prior art BOTDA system.

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

Brillouin optical time-domain analysis ("BOTDA") is one of the common configurations of SBS-based optical fibre sensors. In general terms, in this configuration, a pulsed probe beam and a continuous wave ("CW") pump beam of different frequencies interact through the intercession of an acoustic wave. In essence, the pulse power of the probe laser is transferred to the CW beam emitted by the pump laser when the frequency difference between the lasers is within the local Brillouin gain spectrum ("BGS") of the fibre. The frequency showing the maximum gain in the BGS is called Brillouin frequency shift ("BFS"). The BFS is linearly related to the strain and temperature as:

$$v_B(T,\epsilon) = C_T T + C_\epsilon \epsilon + v_{B_0} \quad (1)$$

where $C_T$ is the temperature coefficient in MHz/°C., T is the temperature, $v_{B_0}$ is the reference Brillouin frequency, $C_\epsilon$ is the strain coefficient in MHz/µε, and ε is the strain.

Studies on optical sensors indicate that there are multiple sources of noise in such systems, such as those originated from the light, optical transmission, and electrical data acquisition systems. Noise degrades the performance of optical sensors by increasing the measurement time and decreasing the range of measurements. The accumulation of the noise present in optical sensors manifests itself as an additive white noise in electrical signals acquired from BOTDA sensors to conduct measurements. As used herein, the term BOTDA signal includes signals acquired from a BOTDA sensor.

In general, BOTDA signals have a very low signal-to-noise ratio ("SNR") due to the limitation on the power of the pulse and CW beams. BOTDA signals are commonly denoised to extract temperature and strain information. A conventional method to improve the SNR of BOTDA signals is ensemble averaging. Ensemble averaging estimates a clean signal (i.e. a corresponding signal that is noise free) by averaging an ensemble of noisy signals. Ensemble averaging assumes that every noisy signal is composed of an identical deterministic signal s(k) and white noise $n_i(k)$:

$$r_i(k) = s(k) + n_i(k) \quad (2)$$

In equation (2), i is the index for each signal in the ensemble i=1, . . . , N (N is the number of signals in the ensemble), and k is the time (sample) index in the observation window k=1, . . . , K (K is the number of samples in the signal). The expression of the ensemble averaging over N noisy signals is given by:

$$y(k) = \frac{1}{N} \sum_{i=1}^{N} r_i(k), k = 1, \ldots, K \quad (3)$$

In one example, a BODTA system similar to that presented in [1] was used to acquire BOTDA signals and characterize their noise components. The hardware setup for this example BODTA system is shown in FIG. 1.

In the setup of FIG. 1, two lasers operate at a nominal wavelength of 1550 nm. A 1 ns pulse, which corresponds to an approximate spatial resolution of 10 centimeters in the optical fibre, is used for this test. The optical fibre is excited with the laser frequency difference in the range of 10.850 GHz to 11.230 GHz with frequency steps of 2 MHz. Brillouin interaction is recorded through a detector monitoring the CW beam and is then sampled using a digitizer operating at a frequency of 2 GHz.

For this experiment, the fibre under test is composed of segments of SLA and SMF28 optical fibres with their length specification listed in Table 1. The fibre is free of strain and maintained at a constant temperature of 22° C. as the measurement is performed.

TABLE 1

Specifications of the fibre under test.

| | | | | | | | | | | | | | | | | |
|---|---|---|---|---|---|---|---|---|---|---|---|---|---|---|---|---|
| | | | | | | Type of fibre | | | | | | | | | | |
| | SLA | SMF 28 | SLA | SMF 28 | SLA | SMF 28 | SLA | SMF 28 | SLA | SMF 28 | SLA | SMF 28 | SLA | SMF 28 | SLA | SMF 28 |
| Length (m) | 10 | 10 | 5 | 10 | 2 | 10 | 1 | 10 | 0.7 | 10 | 0.5 | 10 | 0.3 | 10 | 0.2 | 10 |

FIG. 2a) depicts a normalized BOTDA signal corresponding to the power of the CW beam at a frequency difference of 11 GHz to show how noisy the BOTDA signals can be. The noisy BOTDA signals in this example have an SNR of approximately 11 dB. Such an SNR usually, if not always, makes it impossible to perform direct measurements of temperature or strain. Therefore, for every frequency difference, typically an ensemble of 1000 BOTDA signals is averaged using ensemble averaging. In this example, signals resulting from ensemble averaging have an SNR of approximately 31 dB. This SNR level enables the sensor to perform accurate measurements of temperature and strain at any point along the fibre. FIG. 2b) depicts a normalized denoised BOTDA signal corresponding to the power of the CW beam at a frequency difference of 11 GHz.

As stated in equation (2), at a particular frequency difference, noisy BOTDA signals are composed of a deterministic signal and different realizations of white noise. Assuming that all premises of the ensemble averaging are met, the resulting signal from this method over thousands of noisy signals is an accurate estimation of the deterministic signal. Hence, the noise of signals can be estimated as follows:

$$s(k) = \lim_{N \to \infty} \frac{1}{N} \sum_{i=1}^{N} r_i(k) \Rightarrow n_i(k) = r_i(k) - s(k), \quad (4)$$

$$k = 1, \ldots, K$$

FIGS. 3a), 3b), and 3c) show the typical noise in the acquired signals calculated based on equation (4) for N equal to 10000. FIG. 3 also shows the power spectral densities ("PSDs") of the noise and the deterministic signal. The PSD of the noise is distributed flatly in the frequency domain while the deterministic signal shows most of the power at low frequencies (0 to 100 MHz). If the noise is assumed to be completely white noise under these conditions, one can assume that BOTDA signals collected at a particular frequency difference are the recurrent signals composed of an identical deterministic signal and different realizations of white noise. This assumption allows an adaptive filtering method according to one or more embodiments of the present invention to be introduced to denoise any recurrent signals, particularly those collected from BODTA sensors. As used herein, the term "recurrent signal" includes an electrical signal which includes a deterministic signal and a realization of white noise. It will be understood that in one or more embodiments, methods according to the present invention can be used to denoise a recurrent signal collected from SBS systems in general and are not limited to denoising recurrent signals from BODTA sensors.

In one or more further embodiments, methods according to the present invention can more generally be used to denoise recurrent signals. As used herein, recurrent signals include two or more signals comprising a common deterministic signal, and a realization of white noise, which is different in each signal. The present invention is not limited to signals from optical systems but can be used to denoise recurrent signals from other sources.

Adaptive Noise Cancellation

Figure 4:
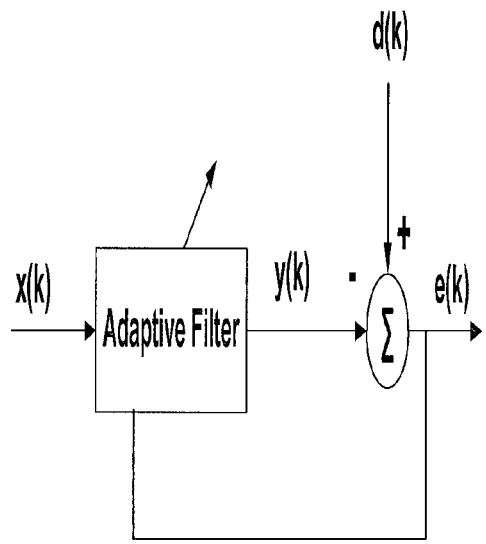
FIG. 4 is a Block diagram of adaptive noise cancellation ("ANC") method.
Figure 5:
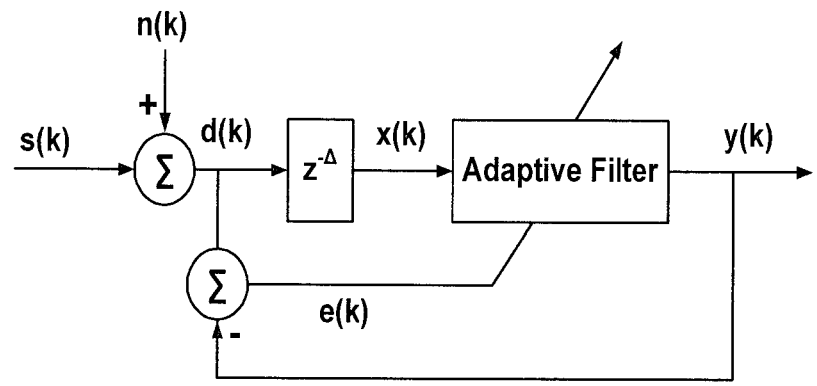
FIG. 5 is a representation of the prior art adaptive line enhancement ("ALE") method.

In general, adaptive noise cancellation ("ANC") methods [2], [3] rely on the use of noise suppression by subtracting noise from a received signal, an operation controlled in an adaptive manner for the purpose of improving the SNR. FIG. 4 is a block diagram of an ANC method taught by Widrow [2] that has x(k) and d(k) as the input and desired signals, respectively. Typically, when using an ANC method to denoise a noisy signal, a noisy signal and noise reference form the desired and input signals, respectively. The Adaptive filter used by Widrow produces an optimal estimation of the noise present in the noisy signal if that noise has correlation with the noise reference. As a result, the error signal e(k), which is the signal resulting from the subtraction of the output of the adaptive filter y(k) from the desired signal d(k), becomes an estimation of the clean signal.

Adaptive Line Enhancement ("ALE") and Adaptive Recurrent Filtering

The ALE technique improves the SNR of signals in the absence of noise reference [4], [5]. It eliminates noise from the signal based on the time coherence differences between the signal and the noise.

5 shows the general scheme of the ALE technique. The delay parameter $\Delta$ is chosen to be smaller than the coherence time of s(k), but larger than the coherence time of n(k). As the result, the adaptive filter predicts only the s(k) from the past samples of d(k−Δ). The ALE technique is also called adaptive linear prediction ("ALP") when Δ is limited to one.

Noise reduction based on ALE improves the SNR of the signal, particularly when the noise is white. Hence, the inventors have applied it to reduce noise in BODTA signals and compare its thresholding capabilities with the other denoising techniques applicable to this type of signals such as the RANC method discussed below.

Recurrent Adaptive Noise Cancellation ("RANC") Methods According to Embodiments of the Present Invention In one or more embodiments of the present invention, two noisy signals (two recurrent signals), $r_1(k)$ and $r_2(k)$ feed the input and desired signals in the ANC method of FIG. 4 which is modified according to the present invention.

The ANC method is a general method introduced by Widrow. The characteristics of the adaptive filter of FIG. 4 change from one application to another. This means there is no predefined filter. Although in this embodiment, the same block diagram (FIG. 4) as Widrow is referenced, the RANC method according to embodiments of the present invention, unlike Widrow, uses two recurrent signals as the input in the method depicted in the block diagram of FIG. 4.

In Widrow, $d(k)=n_2(k)$ and $x(k)=r_1(k)=s(k)+n_1(k)$, where ($n_2(k)$ is an estimation from the noise present in signals, s(k) is a deterministic signal, and $n_1(k)$ is a realization of white noise). One cannot use Widrow's model unmodified for RANC methods according to the present invention because there is no estimation from the noise present in BOTDA signals. Therefore, the inventors applied $d(k)=r_2(k)=s(k)+n_2(k)$ and $x(k)=r_1(k)=s(k)+n_1(k)$ as inputs to RANC methods according to embodiments of the present invention and, in this way, can denoise signals when there is no estimation from the noise present in signals.

The input and desired signals can be expressed as:

$$x(k)=r_1(k)=s(k)+n(k) \quad (5)$$

$$d(k)=r_2(k)=s(k)+m(k) \quad (6)$$

where s(k) is the deterministic signal that is independent of the white noises n(k) and m(k). The noisy signal x(k) is filtered adaptively to provide an estimation of the deterministic signal and the error between the desired signal and estimated signal is calculated as:

$$e(k)=d(k)-y(k)=s(k)+m(k)-y(k) \quad (7)$$

The adaptive filter in this example is not the Widrow filter. It automatically adapts its own impulse response as a reaction to the changes of the error signal. The adaptation process can be achieved with one of several algorithms reported in the literature such as least mean squares ("LMS") [3], normalized least mean squares ("NLMS") [3], recursive least squares ("RLS") [6], affine projection ("AP") [7], fast affine projection ("FAP") [7], fast Newton transversal ("FNT") [8], or Kalman [9]. For the simplest case, with LMS, with adequate tuning to the selected adaptive algorithms, the adaptive filter provides the best estimation of the deterministic signal while minimizing the error [2], [3]. For the LMS algorithm, the square error is calculated as:

$$e^2(k)=(s(k)+m(k)-y(k))^2=(s(k)-y(k))^2+m^2(k)+2m(k)(s(k)-y(k)) \quad (8)$$

The expected value of the squared error can be formulated as equation (9), assuming that m(k) is uncorrelated with s(k) and y(k):

$$E[e^2(k)]=E[(s(k)-y(k))^2]+E[m^2(k)]+2E[m(k)(s(k)-y(k))]=E[(s(k)-y(k))^2]+E[m^2(k)]=E[(s(k)-y(k))^2]+\sigma_m^2 \quad (9)$$

In this equation, $\sigma_m^2$ is the variance of the noise m(k). The adaptive filter does not affect this variance as it is adjusted to minimize $E[e^2(k)]$. Therefore, the minimum error is expressed as:

$$\min E[e^2(k)]=\min E[(s(k)-y(k))^2]+\sigma_m^2 \quad (10)$$

When the adaptive filter is adjusted to minimize $E[e^2(k)]$, it automatically minimizes the error $E[(s(k)-y(k))^2]$. This error minimization makes the output of adaptive filter y(k) the best estimation of the deterministic signal s(k). In this way, the deterministic signal is estimated from the noisy signal in the absence of noise reference.

Figure 6:
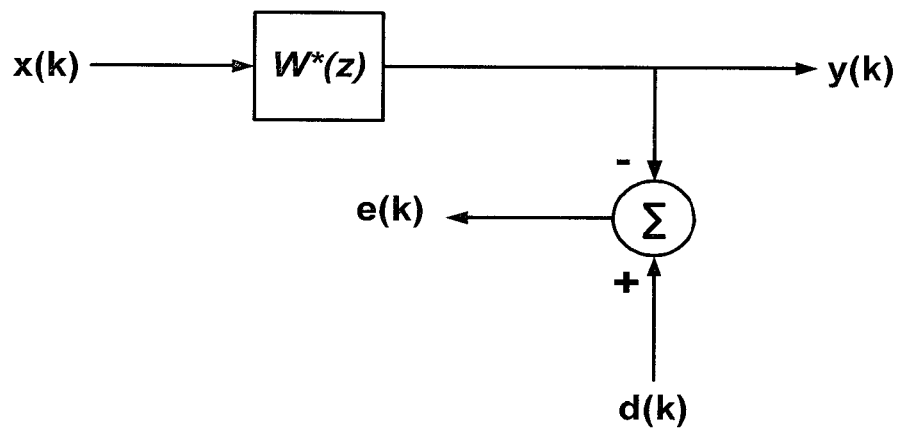
FIG. 6 is a representation of a Single channel Wiener filter.

Wiener Solution for RANC Methods According to Embodiments of the Present Invention FIG. 6 is a block diagram of a single-input single-output Wiener filter modeled for RANC methods according to one or more embodiments of the present invention. In general, an adaptive filtering method is adapted in the time domain until its filter coefficients converge to optimal values. In the literature of adaptive filtering, the optimal state of an adaptive process is called the Wiener solution. This means that RANC methods according to the present invention provide the best results when they are converged to their Wiener solution. In this figure, the notation of signals has the same meaning as those in FIG. 4.

It is assumed that the input and desired signals are statistically stationary. In addition, the filter is considered linear and is designed to be optimum in the minimum mean squares error criterion.

The optimal impulse response W*(k) of the RANC method is calculated in the following way:

The autocorrelation of the input signal x(k) is defined as:

$$r_{xx}(k) \triangleq E[x(j)x(j+k)] \quad (11)$$

The cross-correlation between x(k) and d(k) is similarly defined as:

$$r_{xd}(k) \triangleq E[x(j)d(j+k)] \quad (12)$$

The optimal impulse response is related to the input and desired signals through the Wiener-Hopf equation as:

$$\sum_{j=-\infty}^{\infty} w^*(j) r_{xx}(k-j) = w^*(k) * r_{xx}(k) = r_{xd}(k) \quad (13)$$

The transfer function of the Wiener filter is derived by taking the discrete time Fourier transform ("DTFT") of both sides of equation (13):

$$W^*(\omega) = \frac{P_{xd}(\omega)}{P_{xx}(\omega)} \quad (14)$$

where $P_{xx}(\omega)$ and $P_{xd}(\omega)$ are the PSDs of $r_{xx}(k)$ and $r_{xd}(k)$, respectively. The Wiener filter theory is applied to the RANC problem by assuming that the adaptive process has converged and the minimum mean squares error solution has been found. In the case of estimating the deterministic signal, the auto correlation signal $r_{xx}(k)$ is expressed as:

$$r_{xx}(k) = r_{ss}(k) + r_{nn}(k) = r_{ss}(k) + \sigma_n^2 \delta(k) \quad (15)$$

Moreover, the cross correlation signal $r_{xd}(k)$ is expressed as:

$$r_{xd}(k) = r_{ss}(k) \quad (16)$$

Substituting equation (16) in equation (14) results in the Wiener solution of the RANC approach:

$$W^*(\omega) = \frac{P_{ss}(\omega)}{P_{ss}(\omega) + P_{nn}(\omega)} = \frac{P_{ss}(\omega)}{P_{ss}(\omega) + \sigma_n^2} \quad (17)$$

The resulting Wiener solution is not dependent upon the noise present in the desired signal, but on the deterministic signal and the noise present in the input signal.

Least Mean Squares (LMS) Algorithm

The LMS algorithm is the touchstone used to adjust the coefficients (weights) of the adaptive filter in this invention (the other algorithms such as NLMS, RLS, AP, FAP, FNT, or Kalman can also be applied to adjust weights in the RANC methods) according to the present invention. This algorithm has less computational complexity than other adaptation algorithms and has a potentially good tracking performance [2], [3]. The LMS algorithm adjusts the weights of the adaptive filter under the criterion of minimum mean-squares error.

Figure 7:
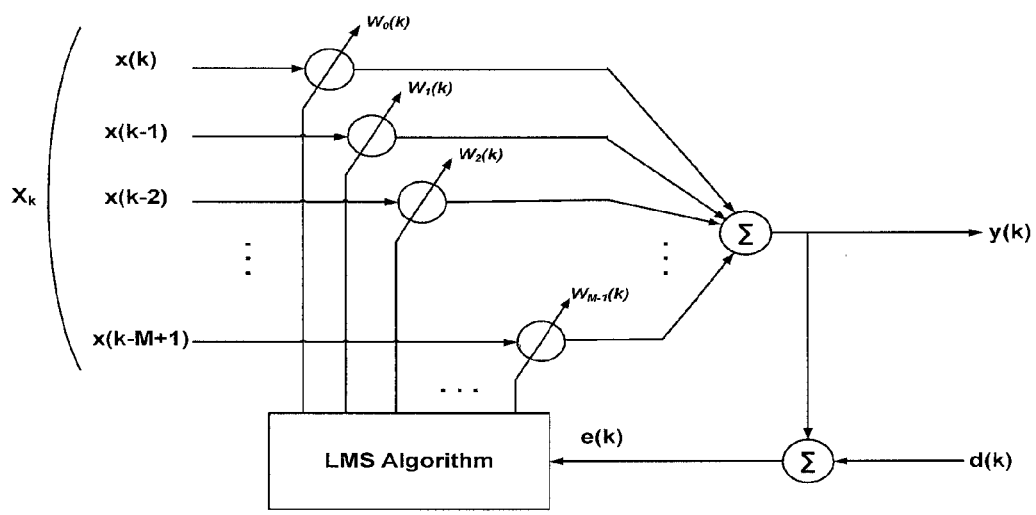
FIG. 7 is a representation of a recurrent adaptive noise cancellation ("RANC") method according to an embodiment of the present invention based on the least mean squares ("LMS") algorithm.

FIG. 7 shows the scheme of a RANC method according to one or more embodiments of the present invention where the adaptive filter is adjusted with the LMS algorithm.

Defining the input samples and the weights of the adaptive filter as vectors, the output of adaptive filter is expressed as the inner product of the vectors:

$$X_k = [x(k), x(k-1) \ldots x(k-M+1)]^T \quad (18)$$

$$W_k = [W_0(k), w_1(k), \ldots, w_{M-1}(k)]^T \quad (19)$$

$$y(k) = X_k^T W_k = W_k^T X_k \quad (20)$$

The size of these vectors is determined by the order of the adaptive filter as M+1. The error signal, which is the difference between the desired signal d(k) and the output signal y(k), is given by:

$$e(k) = d(k) - y(k) = d(k) - X_k^T W_k \quad (21)$$

Based on the LMS algorithm, the adaptive filter updates its weights in time as:

$$W_{k+1} = W_k + 2\mu e(k) X_k \quad (22)$$

In this equation, μ is the step-size parameter that controls the stability and rate of convergence (0<μ≤1). The step-size parameter along with the order of the adaptive filter also affect the convergence time:

$$\tau_{mse} \simeq \frac{M+1}{4\mu} \quad (23)$$

The appropriate value of the step-size parameter and the order of the adaptive filter are selected through experiments based on the characteristics of underlying signals. As the focus of the present invention is not the LMS algorithm, the inventors do not present more details about it. Those of ordinary skill in the art can find more detailed properties of the LMS algorithm in [2], [3].

Examples

Five simulated examples are provided below wherein the performance of the adaptive line enhancement ("ALE"), and RANC methods according to the present invention are compared. Each simulation includes two noisy signals composed of a deterministic signal and different realizations of white noise ($\sigma_n^2=0.2$). In the ALE method, the noisy signals are concatenated to form a signal with a double length. In the RANC methods, one of those noisy signals is considered as the input signal and the other is considered as the desired signal. The noise is suppressed using both ALE and RANC methods, and the results are presented. The results of filtering are compared based on the performance rate, which is calculated in terms of the ratio between the SNRs at the output and at the input of the models:

$$\eta = \frac{SNR_{out}}{SNR_{in}} = \frac{\frac{P_s}{P_{n_{out}}}}{\frac{P_s}{P_{n_{in}}}} = \frac{P_{n_{in}}}{P_{n_{out}}} = \frac{\sigma_{n_{in}}^2}{\sigma_{n_{out}}^2} \qquad (24)$$

In this equation, $P_s$ is the power of the deterministic signal; $P_{n_{in}}$ and $P_{n_{out}}$ are the powers of noise in the input and output signals, respectively; $\sigma_{n_{in}}^2$ and $\sigma_{n_{out}}^2$ are the variances of noise in the input and output signals.

The deterministic signals of the first three examples are chosen to have characteristics such as jumps and smooth pieces, similar to those of the BOTDA signals. The deterministic signal in the fourth example is a sinusoidal signal selected from [10]. In the fifth example, the deterministic signal is an electrocardiograph (ECG) signal selected from MIT-BIH arrhythmia database [11]. The two later examples are conducted to show that the application of RANC technique (methods) according to one or more embodiments of the present invention can be extended to other fields of research in which recurrent signals are encountered.

Ex. 1: The deterministic signal is a ramp waveform given by:

$$s(k) = \begin{cases} \frac{k}{K}, & k \leq 0.37K \\ \frac{k}{K} - 1, & k > 0.37K \end{cases}, K = 600 \qquad (25)$$

Ex. 2: The deterministic signal is a Doppler waveform given by:

$$s(k) = \sin(\pi K/5(k+0.05)), K=600 \qquad (26)$$

Ex. 3: The deterministic signal is a Cusp waveform given by:

$$s(k) = \sqrt{\left|\frac{k}{K} - 0.37\right|}, K = 600 \qquad (27)$$

Ex. 4: The deterministic signal is a sinusoidal waveform selected from the references [10] and is given by:

$$s(k)=\sin(0.06k)\cos(0.01k), K=600 \qquad (28)$$

This example includes two different tests. In the first test, the waveform is contaminated with white noise. In the second test, the waveform is contaminated with nonlinearly perturbed white noise. This kind of noise is used to simulate the noise present in transmission channels as reported in [10], [12] and [13]. The nonlinear noise is generated by applying a nonlinear function such as $n(k)=0.6(n_0(k))^3$ to a white noise source $n_0(k)$. As both ALE and RANC techniques (methods) are based on linear filtering, the second test is expected to have a smaller SNR improvement.

Ex. 5: The deterministic signal is an electrocardiograph (ECG) signal selected from MIT-BIH arrhythmia database [11]. The noisy ECG signal is divided into segments having a single P-QRS-T complex using the QRS detection algorithm presented in [14] and then denoised using both techniques.

The noisy signals of the examples are denoised using the ALE and RANC techniques and the results are depicted in FIGS. 8-13.

The highest performance rate is also calculated versus the filter order for all examples and is listed in Table 2.

TABLE 2

Performance rate versus the filter order for the examples.

| | Performance rate (dB) | | | | | | | | | | | | | | | |
|---|---|---|---|---|---|---|---|---|---|---|---|---|---|---|---|---|
| | ALE | | | | | | | | RANC | | | | | | | |
| | Technique | | | | | | | | | | | | | | | |
| Filter order | 8 | 16 | 24 | 32 | 40 | 48 | 56 | 64 | 8 | 16 | 24 | 32 | 40 | 48 | 56 | 64 |
| Ex. 1 | 12.72 | 13.07 | 12.71 | 12.43 | 12.49 | 12.67 | 12.62 | 12.66 | 15.10 | 15.25 | 15.18 | 15.20 | 15.17 | 15.15 | 15.14 | 15 |
| Ex. 2 | 11.81 | 12.22 | 12.33 | 12.52 | 12.57 | 12.46 | 12.55 | 12.67 | 14.45 | 14.70 | 15.12 | 15.18 | 15.19 | 15.20 | 15.18 | 15.15 |
| Ex. 3 | 13.62 | 15.68 | 16.05 | 16.29 | 16.43 | 16.34 | 16.26 | 16.11 | 17.35 | 18.50 | 18.84 | 18.91 | 18.87 | 18.68 | 18.63 | 18.51 |
| Ex. 4 (test 1) | 10.14 | 11.22 | 11.58 | 11.13 | 10.68 | 10.24 | 9.78 | 9.35 | 12.15 | 12.73 | 12.84 | 12.81 | 12.81 | 12.78 | 12.68 | 12.65 |
| Ex. 4 (test 2) | 2.98 | 3.53 | 4.07 | 5.09 | 5.81 | 6.09 | 6.10 | 6.12 | 7.08 | 7.34 | 7.95 | 8.46 | 8.54 | 8.48 | 8.46 | 8.45 |
| Ex. 5 | 10.72 | 11.54 | 11.47 | 11.46 | 11.67 | 11.94 | 12.38 | 12.62 | 14.57 | 14.26 | 14.05 | 13.84 | 13.84 | 13.75 | 13.81 | 13.65 |

The results of the simulations indicate that RANC methods according to the present invention eliminate a portion of noise from a noisy signal and improve the SNR of a noisy signal. In the simulations of these examples, the RANC methods improved the SNR of a noisy signal on average by 2.6 dB more that the ALE method used to denoise the same signal. In addition, the result of suppression of nonlinear white noise in Ex. 4 indicates that RANC methods according to the present invention can be used to eliminate a significant portion of noise from recurrent signals where the noise is uncorrelated noise.

A signal that has been denoised using a RANC method may still have some residual random noise and distortion. At least some of the residual noise and distortion can be eliminated by applying ensemble averaging to the denoised signal. FIGS. 14a) and 14b) depict the result of averaging an ensemble of 40 signals denoised in Ex. 4 using the ALE and RANC methods where the noise variance is reduced to 6.9×10⁻⁴ and 12.3×10⁻⁴, respectively.

Application of the ALE and RANC Methods to BOTDA Sensors

The original setup used is modified in two ways to evaluate the application of ALE and RANC methods according to certain embodiments of the present invention to BOTDA sensors. The block corresponded to each technique (method) was placed ahead of the ensemble averaging block. As a result, the acquired BOTDA signals are denoised using the ALE or RANC method before applying ensemble averaging (hereafter we call it "setup1" when the ALE technique is evaluated and "setup2" when the RANC technique is evaluated). It is expected that this combination will drastically reduce the number of BOTDA signals required to get an acceptable SNR.

The fibre under test is examined using the original and modified setups and the results are presented. FIG. 15*a*) shows a noisy BOTDA signal corresponding to the power of the CW beam measured at a frequency difference of 10.990 GHz (SNR of 11 dB). An ensemble of 1000 noisy signals is averaged in the original setup to improve the SNR to an acceptable level (31 dB). FIG. 15*b*) shows the resulting denoised signal. The same SNR of 31 dB is achieved in setup1 and setup2 by averaging an ensemble of just 140 and 90 signals, respectively. This reflects that the application of the ALE and RANC techniques reduced the number of collected signals by 86% and 91%, respectively.

To emphasize the differences between the ALE and RANC techniques (methods), the test is conducted for the same number of averaging in setup1 and setup2. The result shows that for the number of averaging of 90, setup1 provides an SNR of 28.5 dB while setup2 provides an SNR of 31 dB. The resulting denoised signals of setup1 and setup2 are depicted in FIGS. 15*c*) and 15*d*), respectively.

The accuracy of temperature and strain measurements in BODTA setups can be assessed by finding the BFS for all points along the fibre. Based on the theory [15], the BFS is located at the central frequency of the BGS. An ideal BGS has a Lorentzian distribution in the frequency domain and can be modeled by:

$$g(v) = \frac{g_B}{1 + 4\left(\frac{v - v_B}{\Delta v_B}\right)^2} \qquad (29)$$

Figure 16:
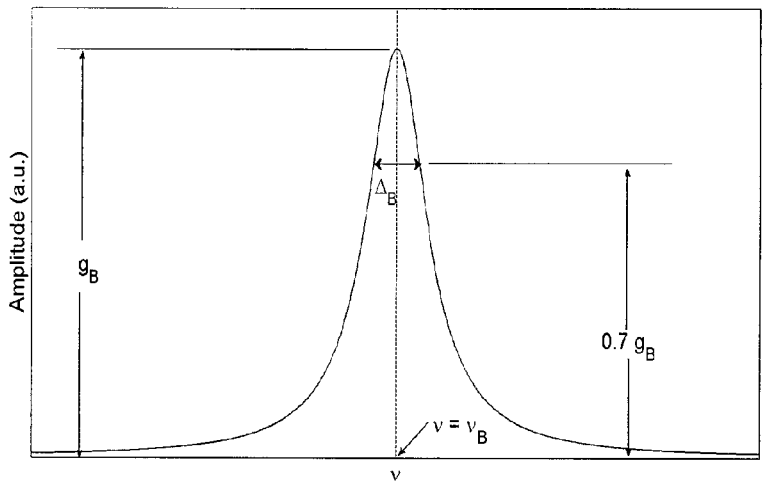
FIG. 16 is an ideal Brillouin gain spectrum (BGS)

Three parameters are required to describe the BGS: the BFS $v_B$, the bandwidth $\Delta v_B$, and the peak gain $g_B$. FIG. 16 shows the ideal BGS along with an illustration of how each parameter is determined.

The BFS is calculated by finding the frequency of the maximum in the ideal BGS but its calculation is not that straightforward in real applications. In effect, the BGSs are noisy and do not have a perfect Lorentzian distribution. For this reason, an ideal Lorentzian curve is fitted to them to estimate their BFS. The accuracy of the results achieved by the curve fitting is directly related to the amount of noise in the BGSs; therefore, the BOTDA signals are denoised to provide accurate results. FIGS. 17*a*), 17*b*), 17*c*) and 17*d*) depict the noisy and denoised BGSs along with the fitted Lorentzian curves at a position of 50 m along the fibre. The results show that all setups found almost the same value for the BFS; however, the original setup required 1000 signals while setup1 and setup2 required 140 and 90 signals, respectively.

The SNR of the spectra (BOTDA signals) was calculated based on the standard formula presented in [16]. In this formula, the SNR of a particular spectrum is defined as:

$$SNR = \frac{S^2}{N^2} = \frac{(g(v_B))^2}{N^2} = \frac{g_B^2}{N^2} \qquad (30)$$

where N is the noise defined as the residual after subtracting the fitted curve from the spectrum.

As the whole fibre was free of strain and maintained at a constant temperature of 22° C. during experiments, it is expected that the BFSs would be constant in similar segments of the fibre. FIGS. 18*a*), 18*b*), and 18*c*)) show the calculated BFSs for the first 70 m of the fibre. As expected, all setups follow almost the same pattern.

Decreasing the number of collected signals yields a major reduction in the measurement time of the BOTDA sensor. This reduction in the measurement time can be explained as follows:

A 1 ns pulse requires 99.7 ns (99.7×1 ns) to scan the fibre with the length of 99.7 m. For a range of frequency differences between 10.850 GHz and 11.230 GHz and a frequency step of 2 MHz, there are 191 frequencies in the data set. Hence, scanning the fibre in all frequency one time takes 19.043 us (191×99.7 ns).

The fibre has been scanned 1000 times in the original setup which makes the measurement time 19.043 ms. In setup1, the measurement time is the summation of the time required to scan the fibre 140 times (2.666 ms) and an additional processing time for the ALE technique. The measurement time of setup2 is the summation of the time required to scan the fibre 90 times (1.714 ms) and an additional processing time for the RANC technique. The additional processing time imposed by using both techniques is negligible as they filter the noise simultaneously with the scanning process. Therefore, the measurement times of setup1 and setup2 become approximately 2.666 ms and 1.714 ms, respectively.

The results of calculating the measurement time demonstrate that the application of ALE and RANC techniques (methods) has reduced the measurement time up to 91%.

Figure 19:
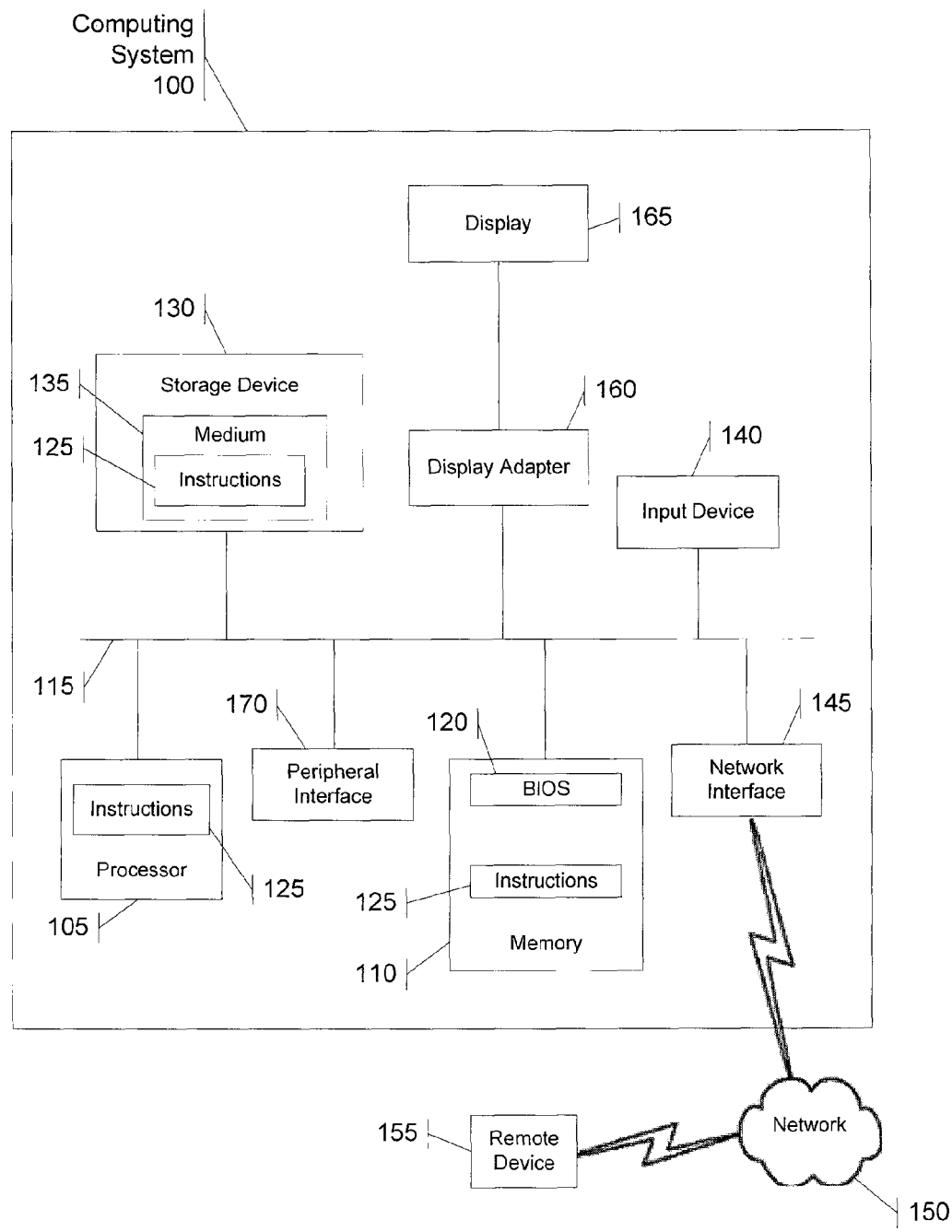
FIG. 19 is an illustration of a general purpose computer system.

A computing system, such as a general purpose computing system or device, may be used to implement embodiments of the present invention wherein within the computing system, there is a set of instructions for causing the computing system or device to perform or execute any one or more of the aspects and/or methodologies of the present disclosure. It is also contemplated that multiple computing systems or devices may be utilized to implement a specially configured set of instructions for causing the device to perform any one or more of the aspects, functionalities, and/or methodologies of the present disclosure. FIG. 19 illustrates a diagrammatic representation of one embodiment of a computing system in the exemplary form of a computer system 100 which includes a processor 105 and memory 110 that communicate with each other, and with other components, via a bus 115. Bus 115 may include any of several types of bus structures including, but not limited to, a memory bus, a memory controller, a peripheral bus, a local bus, and any combinations thereof, using any of a variety of bus architectures.

Memory 110 may include various components (e.g., machine readable media) including, but not limited to, a random access memory component (e.g, a static RAM "SRAM", a dynamic RAM "DRAM", etc.), a read only component, and any combinations thereof. In one example, a basic input/output system 120 (BIOS), including basic routines that help to transfer information between elements within computer system 100, such as during start-up, may be stored in memory 110. Memory 110 may also include (e.g., stored on one or more machine-readable media) instructions (e.g., software) 125 embodying any one or more of the aspects and/or methodologies of the present disclosure. In another example, memory 110 may further include any number of program modules including, but not limited to, an operating system, one or more application programs, other program modules, program data, and any combinations thereof.

Computer system 100 may also include a storage device 130. Examples of a storage device (e.g., storage device 130) include, but are not limited to, a hard disk drive for reading from and/or writing to a hard disk, a magnetic disk drive for reading from and/or writing to a removable magnetic disk, an optical disk drive for reading from and/or writing to an optical media (e.g., a CD, a DVD, etc.), a solid-state memory device, and any combinations thereof. Storage device 130 may be connected to bus 115 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 130 (or one or more components thereof) may be removably interfaced with computer system 100 (e.g., via an external port connector (not shown)). Particularly, storage device 130 and an associated machine-readable medium 135 may provide non-volatile and/or volatile storage of machine-readable instructions 125, data structures, program modules, and/or other data for computer system 100. In one example, software 125 may reside, completely or partially, within machine-readable medium 135. In another example, software 125 may reside, completely or partially, within processor 105.

Computer system 100 may also include an input device 140. In one example, a user of computer system 100 may enter commands and/or other information into computer system 100 via input device 140. Examples of an input device 140 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), touch screen, and any combinations thereof. Input device 140 may be interfaced to bus 115 via any of a variety of interfaces (not shown) including, but not limited to, a serial interface, a parallel interface, a game port, a USB interface, a FIREWIRE interface, a direct interface to bus 115, and any combinations thereof. Input device may include a touch screen interface that may be a part of or separate from display 165, discussed further below.

A user may also input commands and/or other information to computer system 100 via storage device 130 (e.g., a removable disk drive, a flash drive, etc.) and/or a network interface device 145. A network interface device, such as network interface device 145 may be utilized for connecting computer system 100 to one or more of a variety of networks, such as network 150, and one or more remote devices 155 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 150, may employ a wired and/or a wireless mode of communication. In general, any network topology may be used. Information (e.g., data, software 125, etc.) may be communicated to and/or from computer system 100 via network interface device 145.

Computer system 100 may further include a video display adapter 160 for communicating a displayable image to a display device, such as display device 165. Examples of a display device include, but are not limited to, a liquid crystal display (LCD), a cathode ray tube (CRT), a plasma display, a light emitting diode (LED) display, and any combinations thereof. In addition to a display device, a computer system 100 may include one or more other peripheral output devices including, but not limited to, an audio speaker, a printer, and any combinations thereof. Such peripheral output devices may be connected to bus 115 via a peripheral interface 170. Examples of a peripheral interface include, but are not limited to, a serial port, a USB connection, a FIREWIRE connection, a parallel connection, and any combinations thereof.

Figure 20:
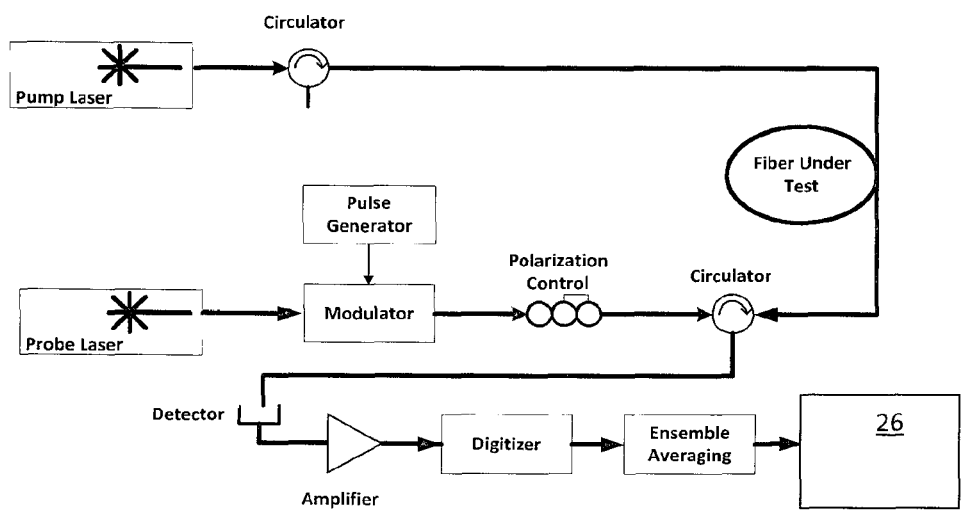
FIG. 20 is a schematic diagram of a BOTDA system according to an embodiment of the present invention.

Methods which embody the principles of the present invention, in one or more embodiments, can be integrated in optical systems such as SBS-based optical fibre sensors, for example a BODTA sensor system of the type illustrated in FIG. 20, as a denoising filter 26 after the ensemble averaging module depicted in FIG. 1. The brillouin analysis sensor system illustrated in FIG. 20 includes a pump laser 2 and a probe laser 4; a first circulator 6 and a sensing fibre 8; the pump laser 2 connected to the first circulator 6 and the first circulator 6 is connected to the sensing fibre 8; a modulator 10, polarization control 12 and a second circulator 14 wherein the probe laser 4 is connected to the modulator 10, the modulator 10 is connected to the polarization control 12, the polarization control 12 is connected to the second circulator 14, and the second circulator 14 is connected to the sensing fibre 8; a pulse generator 16; wherein the pulse generator 16 is connected to the modulator 10; a detector 18, amplifier 20, digitizer 22, ensemble averaging module 24, denoising filter 26 wherein the second circulator 14 is connected to the detector 18, the detector 18 is connected to the amplifier 20, the amplifier 20 is connected to the digitizer 22, the digitizer 22 is connected to the ensemble averaging module 24 and the ensemble averaging module 24 is connected to the denoising filter 26. The denoising filter 26 may also be integrated in another suitable location in the BODTA system, illustrated in FIG. 20, before or after the ensemble filter and may also take another suitable form such as a denoising apparatus or denoising module which may take the form of a computer system programmed to carry out a denoising method according to an embodiment of the present invention.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertain, and those aspects and modifications are within the scope of the invention.

REFERENCES

[1] W. Brown, B. G. Colpitts and K. Brown, "Dark-pulse Brillouin optical time domain sensor with 20-mm spatial resolution," J. Lightw. Technol., vol. 25, no. 1, 381-386, January 2007.

[2] Widrow, J. R. Glover and J. M. McCool, "Adaptive noise cancelling: Principles and applications," Proc. IEEE, vol. 63, no. 12, 1975, pp. 1692-1716.
[3] S. Haykin, "Least-mean-square adaptive filters," adaptive filter theory, 4th Ed. Prentice Hall, 2001.
[4] Kawamura, Y. Iiguni, and Y. Itoh, "A noise reduction method based on linear prediction with variable step-size," IEICE Trans. on Fundamentals of Electronics, Communications and Computer Sciences, vol. 88, pp. 855-861, April 2005.
[5] J. R. Zeidler, "Performance analysis of LMS adaptive prediction filters," Proc. IEEE, vol. 78, no. 12, December 1990, pp. 1781-1806.
[6] S. Haykin, "Recursive Least-Squares Algorithms," adaptive filter theory, 4th Ed. Prentice Hall, 2001.
[7] S. L. Gay, S. Tavathia, "The fast affine projection algorithm," Acoustics, Speech, and Signal Processing, 1995. ICASSP-95, vol. 5, 1995, pp. 3023-3026.
[8] G. V. Moustakides, S. Theodoridis, "Fast Newton transversal filters-a new class of adaptive estimation algorithms," IEEE Trans. Signal Process., vol. 39, no. 10, pp. 2184-2193, 1991.
[9] S. Haykin, "Kalman Filters," adaptive filter theory, 4th Ed. Prentice Hall, 2001.
[10] Provaznik and J. Holcik, "Dynamic adaptive recurrent filter for stress-test ECG processing," Int. Proc. IEEE, 1993, pp. 736-737.
[11] Goldberger et al., "PhysioBank, PhysioToolkit, and PhysioNet: Components of a New Research Resource for Complex Physiologic Signals," Circulation 101(23): pp. e215-e220 [Circulation Electronic Pages: http://circ.ahajournals.org/cgi/content/full/101/23/e215]; 2000 (June 13).
[12] Lin, Li. Chen, D. Yeung, "Adaptive filter design using recurrent cerebellar model articulation controller," IEEE Trans. Neural Netw., vol. 21, no. 7, pp. 1149-1157, July 2010.
[13] Stapleton and S. Bass, "Adaptive noise cancellation for a class of nonlinear dynamic reference channels," IEEE Trans. Circuits Syst., vol. 32, no. 2, pp. 268-271. 1985.
[14] Pan and W. J. Tompkins, "A real-time QRS detection algorithm," IEEE Trans. Biomed. Eng., vol. 32, no. 3, pp. 230-236, 1985.
[15] V. Bortolani et al., "Theory of Brillouin scattering from surface acoustic phonons in supported films," J. Phys. C: Solid State Phys. vol. 16, 1983.
[16] Dhliwayo, J., Webb, D. J, Pannell, C. N, "Statistical analysis of temperature measurement errors in a Brillouin scattering-based distributed temperature sensor," Proc. SPIE, vol. 2838, 1996, pp. 276-286.

We claim:

1. A method of denoising recurrent signals comprising:
providing first and second noisy signals each comprising a deterministic signal and a white noise;
selecting one of the noisy signals as an input signal and the other noisy signal as a desired signal;
providing an estimate of the deterministic signal in the input signal;
determining the error between the estimated deterministic signal and the desired signal;
adjusting the estimate of the deterministic signal using the error; and
producing an adjusted estimate of the deterministic signal.

2. The method of claim 1 wherein the white noise is a different realization of white noise.

3. The method of claim 1 wherein the white noise in the first signal is different from the white noise in the second signal.

4. The method of claim 1 wherein the step of adjusting of the deterministic signal is carried out by minimizing the error using a given criterion.

5. The method of claim 4 wherein the step of minimizing the error is carried out using an error minimization method selected from the group consisting of least mean squares, normalized least mean squares, recursive least squares, affine projection, fast affine projection, fast Newton transversal and Kalman.

6. The method of claim 1 wherein the noisy signals are recurrent signals.

7. The method of claim 6 wherein the recurrent signal is from an optical sensor.

8. The method of claim 7 wherein the optical sensor is an SBS sensor.

9. The method of claim 7 wherein the optical sensor is a BOTDA sensor.

* * * * *